United States Patent [19]
Alexander

[11] Patent Number: 5,894,615
[45] Date of Patent: Apr. 20, 1999

[54] TEMPERATURE SELECTIVELY CONTROLLABLE BODY SUPPORTING PAD

[76] Inventor: Marvin J. Alexander, 159 Guilford St. Extension, Brattleboro, Vt. 05301

[21] Appl. No.: 08/847,657

[22] Filed: Apr. 30, 1997

Related U.S. Application Data

[63] Continuation-in-part of application No. 08/548,148, Oct. 25, 1995, abandoned.

[51] Int. Cl.$^6$ .............................. A47C 21/04; F28F 7/00; F25B 29/00
[52] U.S. Cl. ............................ 5/421; 5/284; 165/46; 165/61; 165/63; 165/64
[58] Field of Search ................... 165/46, 61, 63, 165/64; 607/104; 5/421, 422, 284, 903

[56] References Cited

U.S. PATENT DOCUMENTS 1,896,953  2/1933  Hassell ............................ 607/104
3,007,473  11/1961  Jackson ........................... 607/104
3,894,213  7/1975  Agarwala ......................... 165/46
3,918,458  11/1975  Nethery .......................... 607/104
4,026,299  5/1977  Sauder ........................... 607/104
4,459,468  7/1984  Bailey.

*Primary Examiner*—Flemming Saether
*Attorney, Agent, or Firm*—J. Bradley Cohn

[57] ABSTRACT

A bed pad has embedded in it a circuit of continuous tubing. Portable heating and refrigerating means are operatively connected to a second tubing circuit by quick disconnect couplings. Electrical control means are selectively operated to heat or cool the liquid in said second tubing circuit. Thermostatic controls may optionally be applied to both the heating and refrigerating means. This has particular use in surgical operating rooms for raising and lowering the temperature of the patient. It is also useful in the recovery room, hospital and or convalescent home.

11 Claims, 4 Drawing Sheets

COMPONENT LAYOUT

MATTRESS LAYOUT TO FIT HOSPITAL TYPE BED

COMPONENT LAYOUT

TEMPERATURE SELECTIVELY CONTROLLABLE BODY SUPPORTING PAD

BACKGROUND OF THE INVENTION

This invention is a continuation-in-part of my application for a Seasonal Bed Ser. No. 08/548,148 filed Oct. 25, 1995 and now abandoned.

This invention relates to a heating and cooling system used in bedding and/or a heating and cooling system used for a person lying in bed or on a hospital operating pad. In the preferred embodiment the invention contemplates portability for such a system. While the invention can be used in the home for ordinary comfort it is more particularly useful in hospitals and in surgical operating rooms where it is important to control the patients temperature, accordingly the device provides for selective alternative heating or cooling of the mattress or pad on which the patient or person reclines. While hot and cold water beds are known, the inertia of heating the large reservoir of water in a water mattress does not permit quick changes frequently necessary particularly with an ill patient or a patient in surgery. Thermal blankets such as shown in the patents to Jepson U.S. Pat. No. 2,753,435 and Nicholson U.S. Pat. No. 5,165,127 are not suitable for use with an ill patient because of the weight on top of him or for a patient in surgery since it would prohibit the operative techniques of the surgeon and his or her assistants.

As is well known in hospital surgery the control of the patients temperature usually is the responsibility of the anaesthetist and various means are used to do this ranging from cooling ice packs to warming heat pads. In some procedures the patients blood is circulated through a warming or cooling device. Such methods are cumbersome and frequently even delay operating procedures. Techniques employed in the recovery room following surgery generally involve raising the patients temperature with warm blankets, heating pads and the like. With my invention it may not always be necessary to raise the patients temperature in the recovery room since it can be maintained in the operating room.

Operating rooms themselves are usually at a temperature of about 72 degrees Fahrenheit which while it may be a comfortable for those operating, will not warm a patient whose temperature has dropped precipitously or in certain occasions will not cool a patient whose temperature has risen precipitously.

It is therefore a main object of the present invention to provide quick changing heating or cooling capability in a pad underlying a patient in the surgical room or in the recovery room.

It is another object of my invention is to provide a pad usable on hospital beds whereby patients may be warmed or cooled selectively by attaching my portable system to a pad made in accordance with my invention.

Still another object of my invention is to provide a system that can be made portable so as to allow moving a patient from one location to another.

Other objects will become self evident from further description of the invention.

SUMMARY OF THE INVENTION

This invention provides for a system for selective alternative heating or cooling of a bed pad or mattress. These objects will be apparent from the following descriptions of preferred embodiments when considered along with the accompanying drawings.

The powered unit may be installed in a transportable cabinet and readily connected or disconnected from the pad or mattress or pad. The system is a closed circuit for a fluid and has means to selectively heat or cool said fluid. In the preferred embodiment the fluid is water which is circulated through heating and cooling means that are alternately operable. Both the heating (coils or cal-rods) and cooling means (refrigerant unit) are preferably electrically powered. The amount of water is relatively small in the closed circuit and is thereby quickly warmed or cooled as may be readily understood.

DETAILED DESCRIPTION

Figure 3:
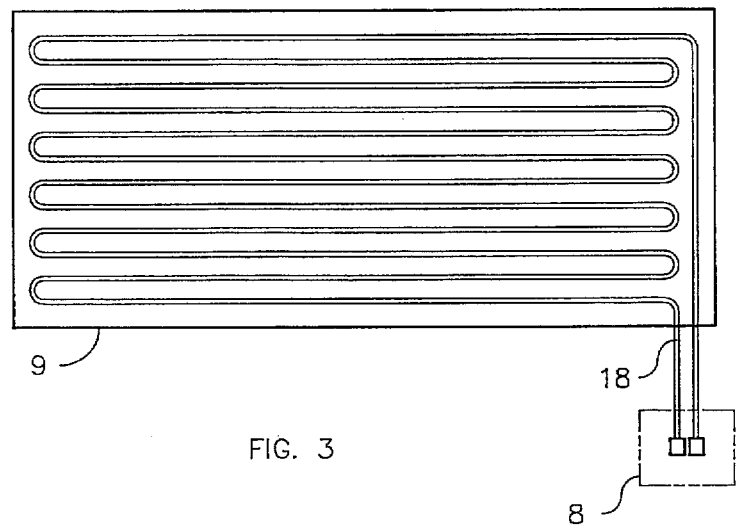
FIG. 3 is a plan diagrammatic view showing the conduits in the pad.
Figure 1:
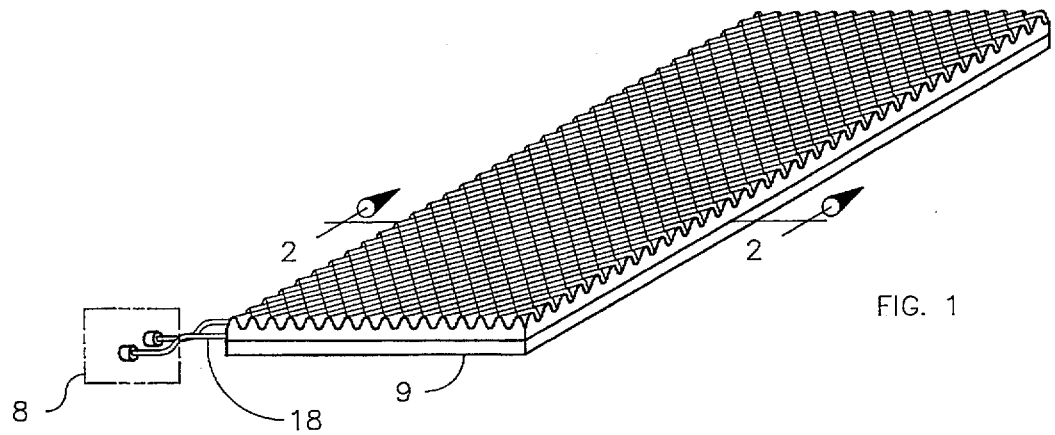
FIG. 1 is a perspective view of a pad or mattress constructed in accordance with the invention.
Figure 2:
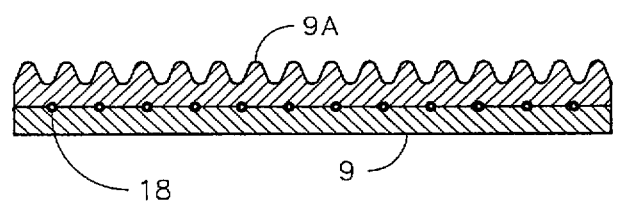
FIG. 2 is a sectional elevation taken in the line 2—2 of FIG. 1.

Referring to FIGS. 1, 2 and 3 the body supporting pad 9 has embedded therein the fluid circulatory tubing, channels or conduits 18, that conduct the cooling or heating fluid. Tubing or channel 18, is positioned within the pad 9 in such a manner as to effectively heat or cool pad 9. FIG. 2, illustrates the relationship of channels 18, within pad 9. Preferably pad 9 has the ridges or papillae 9A to support the patient and provide spacing from tubing 18 as well as air circulation around the patient. FIG. 3 shows a preferred plan view of the layout of tubing 18 in pad 9. Quick disconnection couplings are shown schematically at 8 in FIGS. 1, 3 and 4. The couplings may be of any type well known in the piping and plumbing arts, but preferably are the quick disconnect self sealing type.

Figure 4:
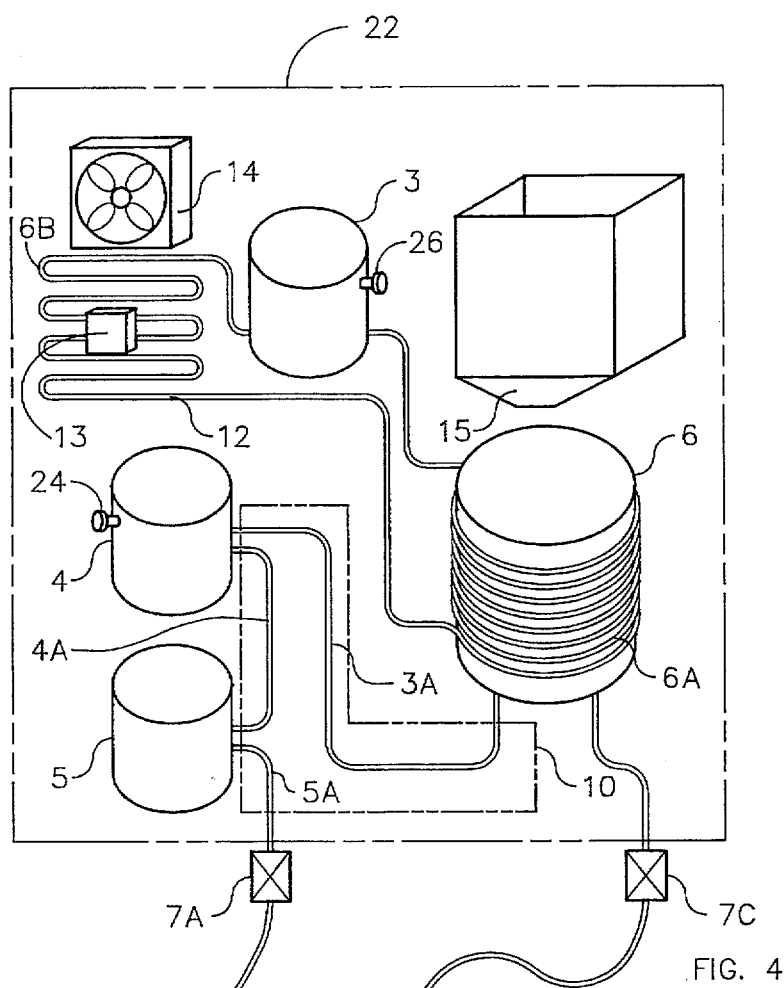
FIG. 4 is a schematic showing of a preferred embodiment of the invention.
Figure 4:
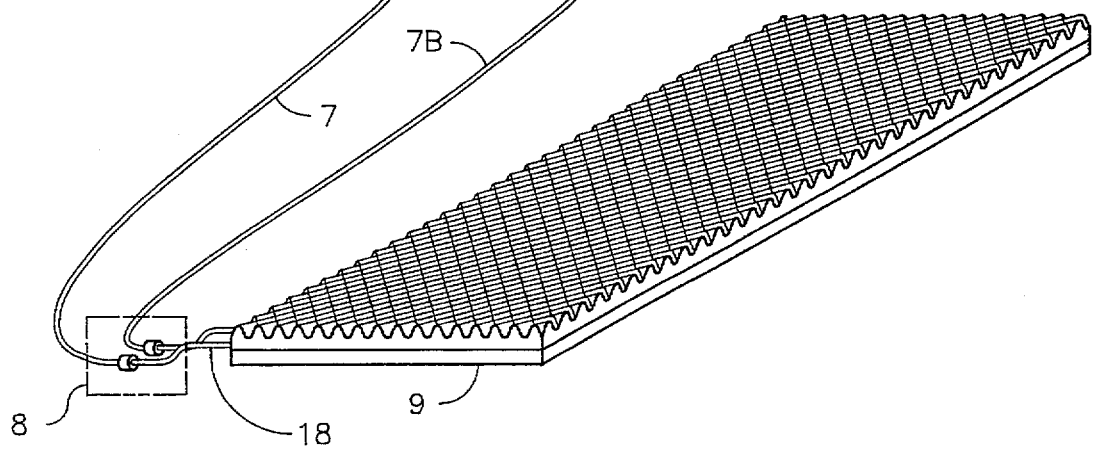

Referring now to FIG. 4, the reservoir 6 contains fluid to be circulated to the pad through the tubes or channels 7, 7B and conduit 18 forming a closed circuit. Optionally the manual valves 17 may be employed, but this is not necessary if the couplings at 8 are of the self sealing type when uncoupled.

When it is desired to warm pad 9, water or other fluid from reservoir 6 is forced through conduit 3A to heater 4 and then through conduit 4A, by pump 5 through the conduit 5A thence through the conducting means or pipe 7 into conduit 18. Then return through conducting means or tubing 7B to reservoir 6. Optionally the pipe 7 may have the manual valve 7A while tubing 7B has the manual valve 7C. Preferably these tubes 7 and 7B communicate respectively with conduit 18 by means of quick disconnect self sealing coupling schematically shown at 8. The self sealing couplings reduce the need for valves 7A and 7C.

Figure 6:
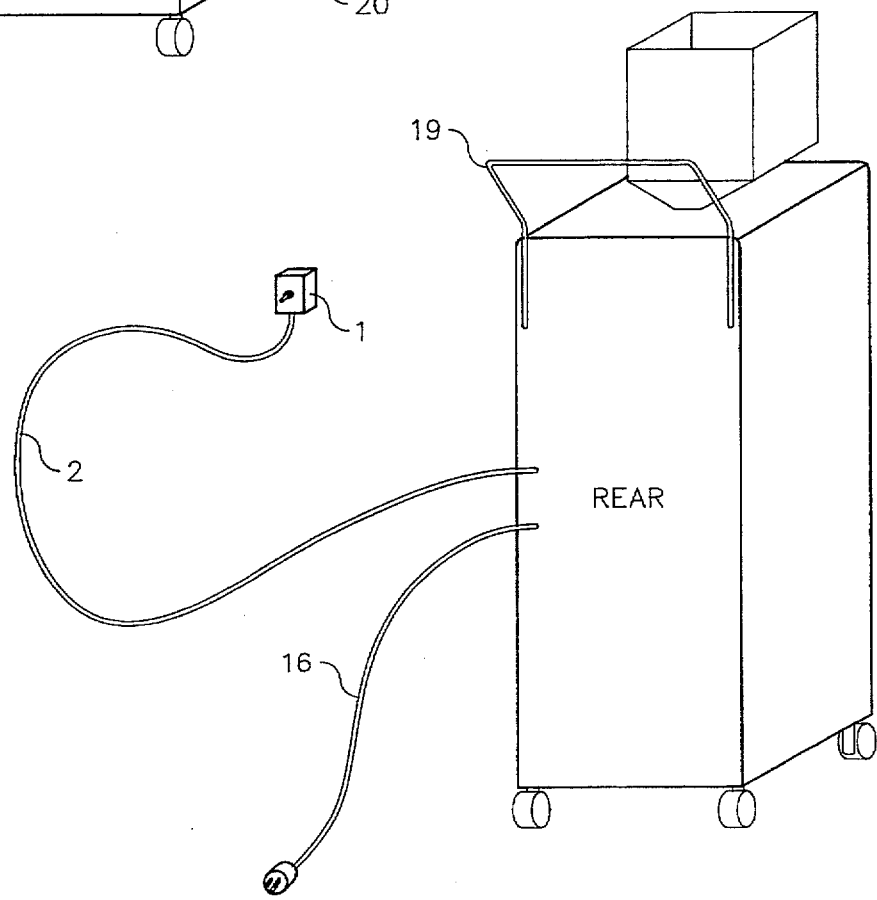
FIG. 6 is a rear view of the same showing the switch for alternative selection of heating and cooling mechanisms.

When it is desired to cool the fluid in pad 9, the toggle switch 1, FIG. 6, is switched and through well known electrical switching controls such as American control No. MR3000. The heater 4 is disengaged and compressor 3 is activated forcing refrigerant through compressor (hot) coils 6B and thence to evaporator coils (cold) 6A and return to low pressure side of compressor 3. To assist cooling the compressor coils, a fan 14 is activated by thermostat 13.

Figure 5:
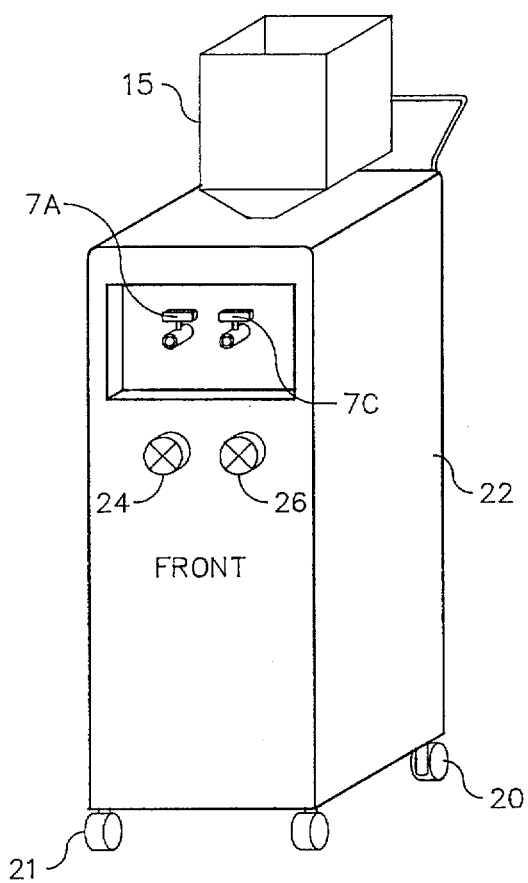
FIG. 5 is a perspective view of a cabinet containing the power and control devices.

Both the compressor 3 and the heater 4 may be modulated FIGS. 4 and 5 by thermostats 26 and 24 respectively.

Heated or cooled conduits 3A, 4A and 5A are indicated schematically at 10.

A reserve or auxiliary reservoir 15 is supplied to fill reservoir 6 as the need arises. Reservoir 15 preferably has a larger capacity than reservoir 6.

Figure 7:
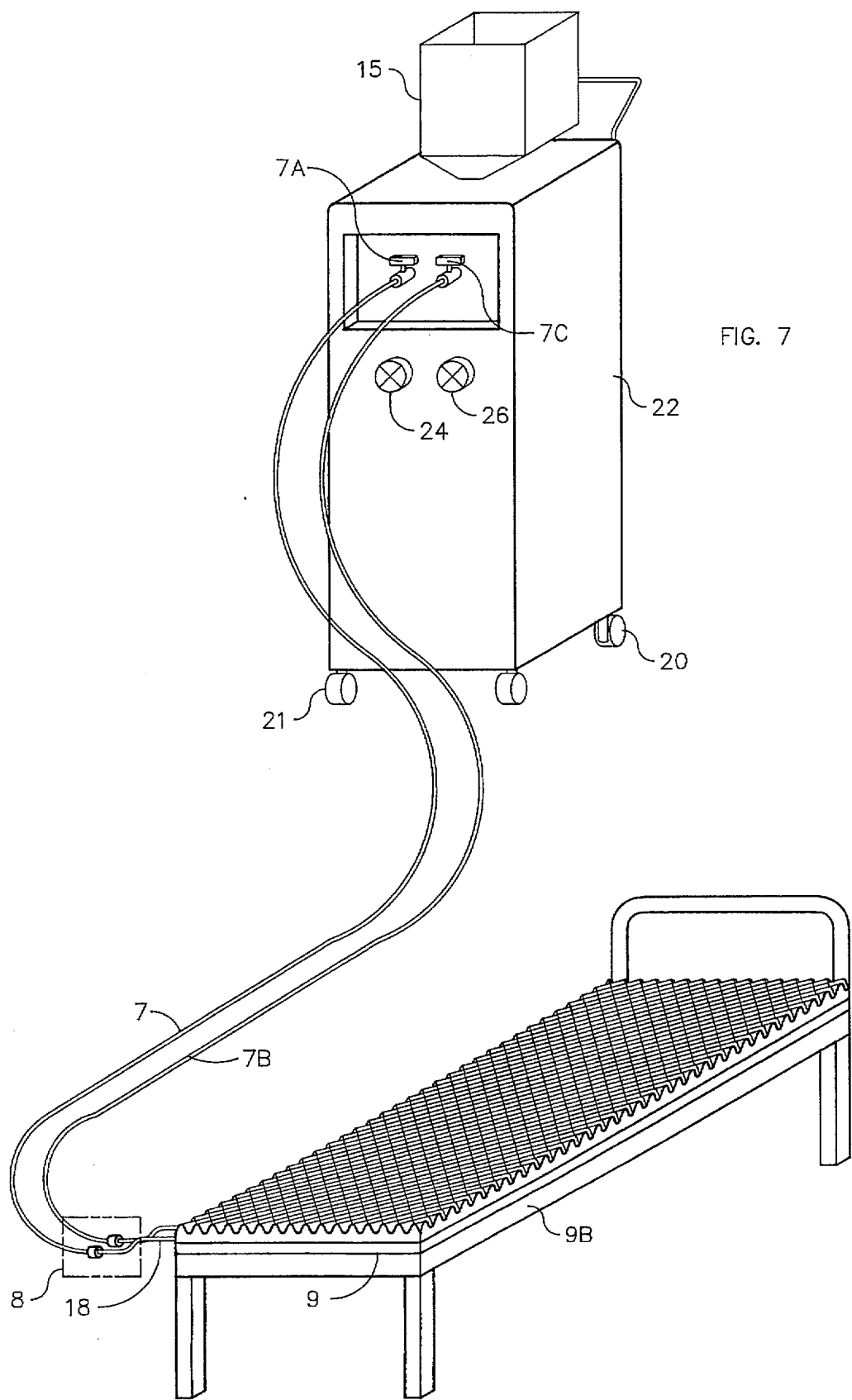
FIG. 7 illustrates the cabinet with FIGS. 5 & 6 connected to the mattress or pad on the bed or gurney.

Referring to FIGS. 5, 6, and 7, the components of the heating and cooling systems may be housed in the portable cabinet 22 having rollers 20 and 21. Valves 7A and 7C if employed may be mounted on the outside face of the cabinet as well as thermostat controls 24 and 26. The pad 9 is shown on the bed 9B in operative fashion. It will be understood that the cabinet 22 may be moved to other pads 9 or moved with the patient if pad 9 is placed on a gurney (not shown) or an operating table (not shown).

The dimensions shown in the drawings are not essential to the invention and applicant reserves the right to remove them from the final formal drawings on allowance of the application.

There is thus provided a unique device for controlling the temperature of a mattress or pad. It is obvious that there are a number of variations for carrying out the intended scope of the invention.

What is claimed is:

1. In combination at least one body supporting pad and a portable temperature controlling device comprising: a conduit embedded in said at least one body supporting pad, means for selectively connecting the portable temperature controlling device said conduit in said at least one body supporting pad, a fluid circulating between the conduit embedded in the pad and the portable temperature controlling device, said portable temperature controlling device comprising: in fluid communication a first reservoir, a heater and a pump, wherein said pump forces said fluid though said first reservoir, said heater and said conduit embedded in the pad, a refrigeration means including a compressor, compressor coils and evaporation coils wherein said evaporating coils are operatively associated with said fluid reservoir to refrigerate the fluid in said reservoir, a control means to alternatively and selectively operate said heater and said refrigeration means so that said fluid is heated or refrigerated to heat or cool the pad through the fluid communication therewith.

2. The invention as set forth in claim 1 further characterized in that said temperature controlling device is mounted in a self contained cabinet having rollers attached hereto.

3. The invention as set forth in claim 1 further characterized in that said refrigerating means has compressor coils and means for circulating air over said compressor coils.

4. The invention as set forth in claim 1 and further characterized by shutoff valves in the connecting means.

5. The invention as set forth in claim 1 and further characterized by an auxiliary reservoir to augment said first reservoir said auxiliary reservoir having a larger capacity than said first reservoir.

6. The invention as set forth in claim 1 wherein said pad is an eggcrate style foam mattress having papillae on it's upper surface.

7. The invention set forth in claim 1 further characterized in that said pad is formed of foam and has ridges formed on it's upper surface.

8. The invention as set forth in claim 1 and is further characterized by thermostatic controlled means controlling said compressor.

9. The invention as set forth in claim 1 characterized by thermostatic controlled means controlling said heating means.

10. The invention as set forth in claim 1 and further characterized in that the connecting means includes quick disconnect type couplings.

11. The invention as set forth in claim 10 and further characterized in that said couplings are self sealing disconnectable types.

* * * * *